United States Patent
Schnaars et al.

(10) Patent No.: US 9,186,478 B2
(45) Date of Patent: Nov. 17, 2015

(54) FILLING DEVICE FOR AN ANESTHETIC DISPENSER

(75) Inventors: Henryk Schnaars, Lübeck (DE); Thomas Lutter, Lübeck (DE); Michael Heidscmidt, Lübeck (DE); Franz Mair, Lübeck (DE); Sven Pasdzior, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 808 days.

(21) Appl. No.: 13/239,738

(22) Filed: Sep. 22, 2011

(65) Prior Publication Data

US 2012/0192992 A1 Aug. 2, 2012

(30) Foreign Application Priority Data

Feb. 2, 2011 (DE) .......................... 10 2011 010 035

(51) Int. Cl.
*A61M 16/18* (2006.01)
(52) U.S. Cl.
CPC .......... *A61M 16/183* (2013.01); *A61M 2205/43* (2013.01)
(58) Field of Classification Search
CPC .................................................... A61M 16/183
USPC .............. 141/18, 94, 326, 346, 351; 220/378, 220/293, 295, 304
See application file for complete search history.

(56) References Cited

U.S. PATENT DOCUMENTS

| | | | | |
|---|---|---|---|---|
| 3,913,783 | A | * | 10/1975 | Cooper .......................... 220/300 |
| 4,081,102 | A | * | 3/1978 | Sakai ........................ 220/203.24 |
| 4,304,339 | A | * | 12/1981 | Sakai et al. ............... 220/203.18 |
| 5,505,236 | A | * | 4/1996 | Grabenkort et al. .......... 141/329 |
| 5,638,975 | A | * | 6/1997 | Harris ............................ 220/288 |
| 6,079,584 | A | * | 6/2000 | Griffin .......................... 220/296 |
| 6,755,316 | B2 | * | 6/2004 | Ono et al. ..................... 220/304 |
| 2008/0236580 | A1 | | 10/2008 | Shang et al. |
| 2010/0319695 | A1 | | 12/2010 | Freed et al. |

FOREIGN PATENT DOCUMENTS

| | | | | |
|---|---|---|---|---|
| CA | 622 821 | A | 6/1961 | |
| DE | 923500 | C | 2/1955 | |
| EP | 348019 | A1 | 12/1989 | |
| EP | 915273 | A2 * | 5/1999 | ............... F16J 16/12 |
| GB | 2436947 | A | 10/2007 | |
| WO | 92/12753 | A1 | 8/1992 | |
| WO | 2007/103658 | A2 | 9/2007 | |
| WO | 2009/117529 | A2 | 9/2009 | |

* cited by examiner

*Primary Examiner* — Timothy L Maust
*Assistant Examiner* — Timothy P Kelly
(74) *Attorney, Agent, or Firm* — McGlew and Tuttle, P.C.

(57) ABSTRACT

A filling device for an anesthetic dispenser has a closing element (3) that can be inserted into the filler neck (2) and can again be removed from same in a simple manner. A bayonet catch is provided between the closing element (3) and the filler neck (2) combined with a ring seal (18). The a ring seal (18) can be pressed in an axial direction by axial rotation and has an elastically deformable spring element.

9 Claims, 6 Drawing Sheets

FILLING DEVICE FOR AN ANESTHETIC DISPENSER

CROSS REFERENCE TO RELATED APPLICATIONS

This application claims the benefit of priority under 35 U.S.C. §119 of German Patent Application DE 10 2011 010 035.0 filed Feb. 2, 2011, the entire contents of which are incorporated herein by reference.

FIELD OF THE INVENTION

The present invention pertains to a filling device for an anesthetic dispenser with a filler neck for liquid anesthetic and a closing element that can be attached to the filler neck by means of a threaded connection.

BACKGROUND OF THE INVENTION

A filling device of this type is known from CA 622 821 A. The anesthetic evaporator operating according to the bypass principle has an evaporating chamber, which is filled with liquid anesthetic. Wicks, which dip into the liquid anesthetic, generate a saturated concentration of anesthetic vapor within the evaporating chamber. A filling device for the anesthetic in the form of a filler neck, which is provided with a closing element that can be screwed in, is located on the outside of the evaporating chamber. To replace consumed anesthetic, the closing element is screwed out of the filler neck and anesthetic is filled into the evaporating chamber. The closing element is also used to seal the evaporating chamber in a pressure-sealed and gas-tight manner against the environment after filling. The drawback of the prior-art closing element is that several turns are needed for closing.

It is also known, as can be determined from EP 348 019 A1, that a sealing ring, which is pressed axially, can be provided between the closing element and the filler neck. Since nearly all elastomeric sealing materials tend to swell under the effect of anesthetic vapor, it is sometimes necessary to apply high torques to loosen the closing element.

Bayonet catches in anesthetic dispensers are also known, DE 923 500 C, but the sealing problems have not been solved satisfactorily.

SUMMARY OF THE INVENTION

A basic object of the present invention is to improve a filling device of the mentioned type such that the closing element can be inserted into the filler neck and again removed from same in a simple manner.

According to the invention, a filling device is provided for an anesthetic dispenser. The filling device comprises a filler neck for liquid anesthetic and a closing element that can be attached to the filler neck by means of a threaded connection. The threaded connection is designed as a rotatingly movably actuatable bayonet catch. A ring seal is pressed by the axial rotation. The ring seal has an elastically deformable spring element provided between the closing element and the filler neck.

The advantage of the device according to the present invention is that the threaded connection between the filler neck and the closing element is designed as a bayonet catch, which is locked or released with a plugging rotary motion. In addition, a ring seal, which can be pressed by the axial rotation of the bayonet catch and which consists of a sealing material and has an elastically deformable spring element, is provided in the connection area of the filler neck and of the closing element. The bayonet catch comprises a bayonet groove at the filler neck and bayonet cams designed correspondingly thereto at the closing element. Polymers, preferably synthetic polymers, for example, those based on carbon, are suitable for use as sealing materials. The bayonet groove is provided with a thread pitch in such a way that the ring seal is pressed axially in the blocked position of the bayonet catch and the closing element is sealed as a result within the filler neck. The axial pressing of the ring seal takes place within the spring deflection preset by the spring element. The spring element consists of metal or an anesthetic-resistant plastic, so that only elastic restoring forces are to be overcome during the axial pressing and swelling effects of the sealing material are of secondary importance. The maximum possible spring stroke can be determined on the basis of the maximum possible angle of rotation of the closing element up to the blocked position and the thread pitch of the bayonet groove and the ring seal is selected to be such that the maximum possible spring stroke is in the elastic deformation range of the ring seal. The bayonet catch combined with the ring seal provided with a spring element has the advantage that the maximum angle of rotation of the closing element for releasing and blocking is limited in such a way that the spring element is deformed only elastically within the ring seal.

The spring element of the ring seal advantageously has a design that is open on one side with two legs and is, for example, V- or U-shaped. Helical or plate-shaped designs are also suitable for the spring element. A free space, which is reduced during the axial elastic pressing of the ring seal, is present between the legs in the undeformed state of the spring element. The axial force to be applied can be affected by selecting the spring rigidity of the spring element. The closing element is advantageously plugged into the filler neck in a first position and is brought by a rotary motion into a second position, in which the closing element is blocked in the filler neck.

A means for acoustic signaling at the time of reaching the second position is advantageously provided. This means may be a catch, which is actuated by one of the bayonet cams when the second position is reached and generates by means of a spring mechanism a clicking sound, which indicates the blocked position. The user thus obtains information that the closing element is locked within the filler neck.

The ring seal is advantageously arranged between a front side of the closing element and a contact surface at the filler neck.

An exemplary embodiment of the device according to the present invention is shown in the drawings and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
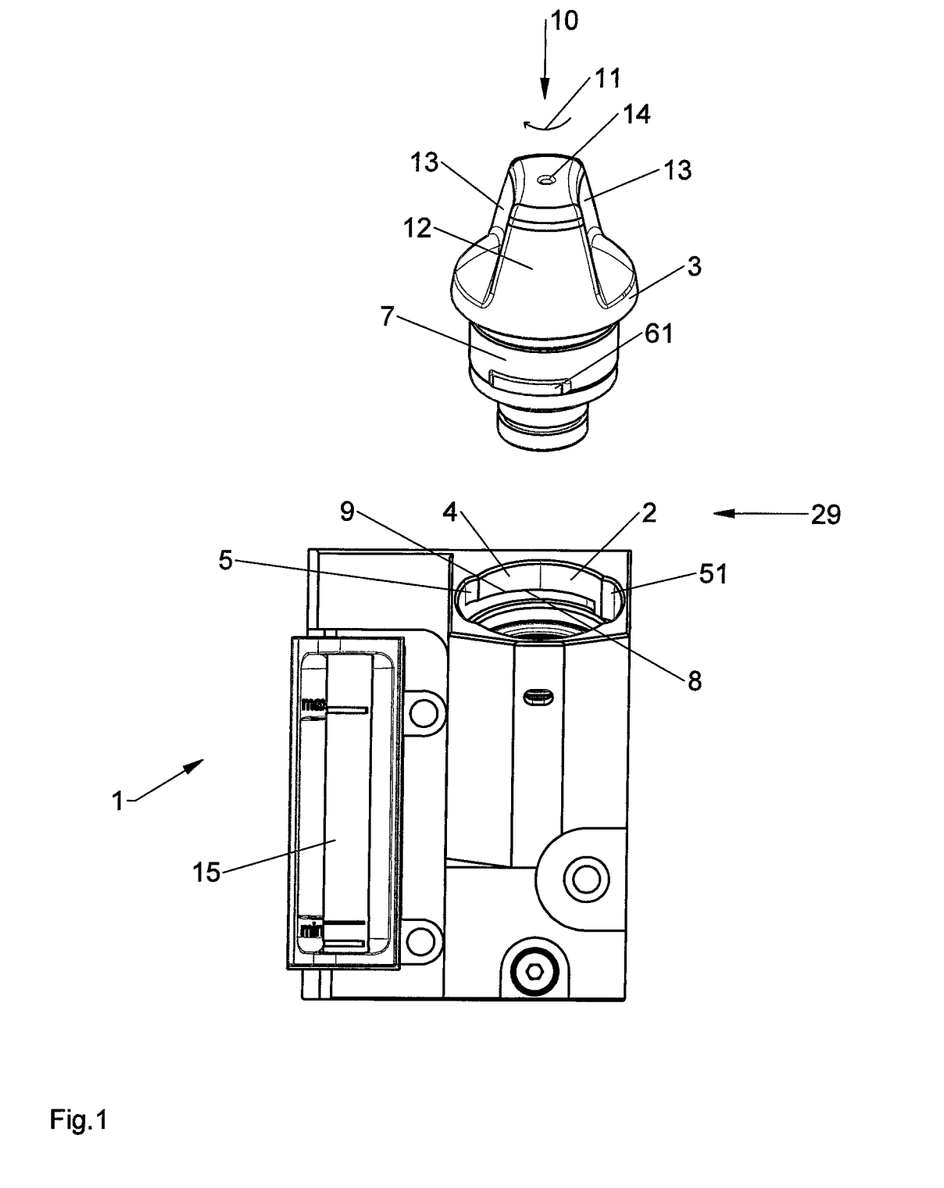
FIG. 1 is a perspective view showing a filling device with a closing element positioned above the filler neck according to the invention.

Referring to the drawings in particular, FIG. 1 shows a filling device 1 with a filler neck 2 for connecting a reservoir for liquid anesthetic, not shown specifically, and with a closing element 3, which can be inserted into the filler neck 2. The filler neck 2 has a cylindrical inner wall 4 with two recesses 5, 51 arranged offset by 180 degrees for inserting two bayonet cams 6, 61, which have a design corresponding thereto and which are arranged at a cylindrical shaft 7 of the closing element 3. Bayonet cam 6 is not shown in FIG. 1, since it is located opposite the bayonet cam 61. For greater clarity, the closing element 3 is shown in FIG. 1 rotated by 90 degrees in relation to the position of the recesses 5, 51 of the filler neck 2. Bayonet grooves (thread parts) 8, 81, which are provided with a thread pitch 9, 91 and have dimensions corresponding to those of the bayonet cams (complementary thread parts) 6, 61, are located on the underside of the recesses 5, 51. Only one of the bayonet grooves, namely, bayonet groove 8, is shown in FIG. 1 for the sake of greater clarity. The closing element 3 is plugged in a first position 10 in the filler neck 2 by the bayonet cams 6, 61 being inserted into the recesses 5, 51 and being brought by a quarter turn, during which the bayonet cams 6, 61 slide in the bayonet grooves 8, 81, into a second position 11, in which the closing element 3 is blocked in the filler neck 2. The closing element 3 has on the top side a toggle-like actuating knob 12 with two opposite grip surfaces 13, as a result of which a rectangular surface 14 is formed on the top side of the actuating knob 12. The rectangular surface 14 makes it possible for the user to recognize the angular position of the closing element 3 in relation to the filler neck 2. When the grip surfaces 13 are located in the drawing plane, this corresponds to the first position 10 of the closing element 3, in which the latter is plugged into the filler neck 2. The surface is rotated by 90 degrees in relation to the starting position in the second position 11 of the closing element 3. The thread pitch 9, 91 of the bayonet grooves 8, 81 causes the closing element 3 to be screwed into (axial movement) the filler neck 2 during the transition (during rotation of closing element 3) from the first position 10 into the second position 11. Together with the bayonet grooves 8, 81 at the filler neck 2, the bayonet cams 6, 61 at the closing element 3 form a bayonet catch 29. In addition to the filler neck 2, a sight glass 15, from which the filling level of the liquid anesthetic in a reservoir, not shown specifically, can be read, is located at the filling device 1.

Figure 1A:
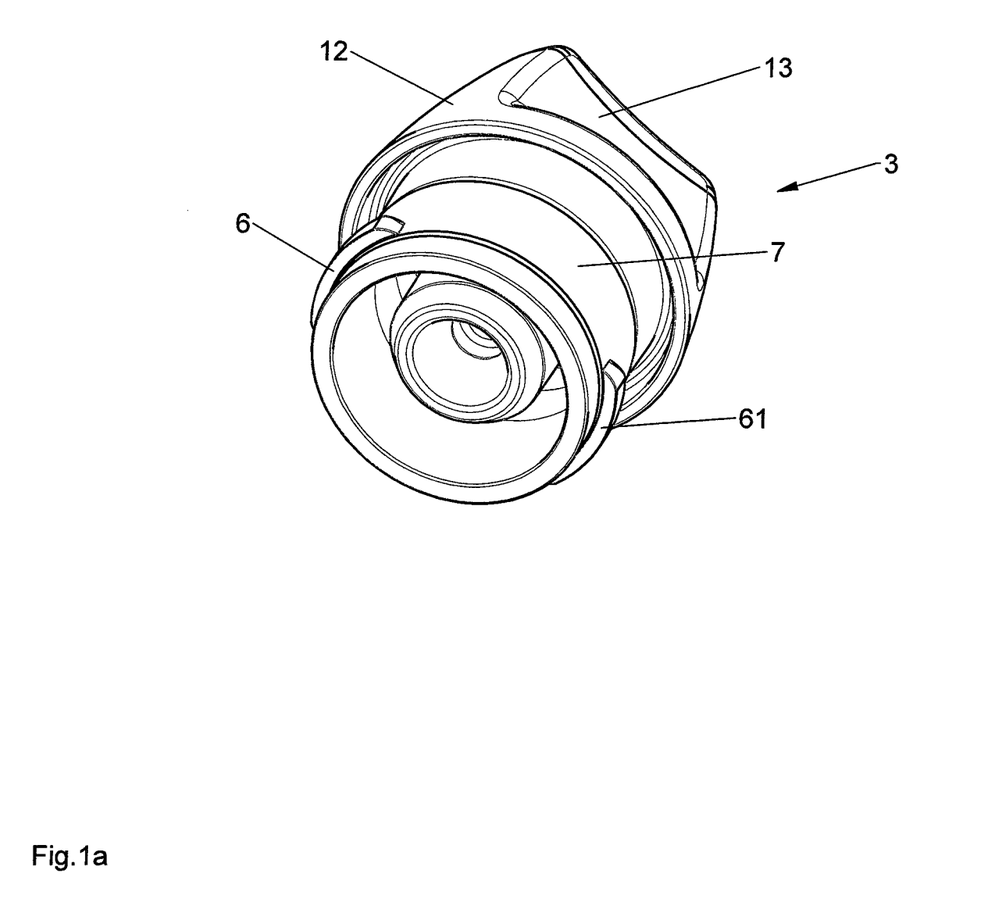
FIG. 1a is a perspective view of the closing element.

FIG. 1a shows as a first addition to FIG. 1 a perspective view of the closing element 3 with the view towards the bayonet cams 6, 61.

Figure 1B:
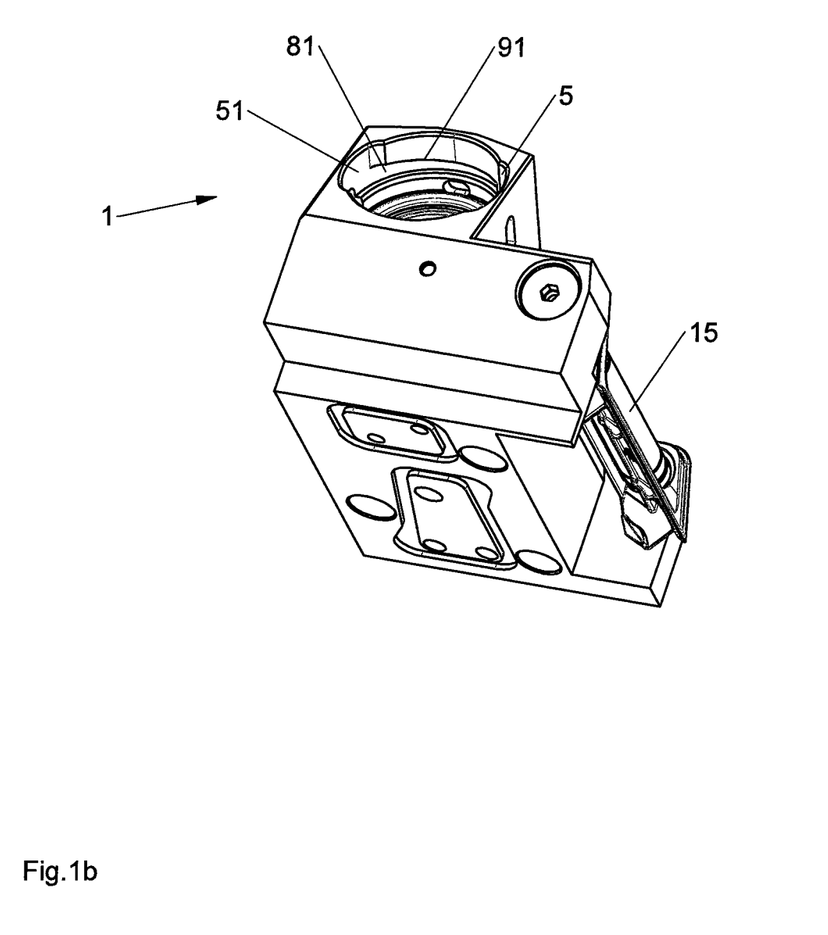
FIG. 1b is a perspective view of the filling device.

FIG. 1b shows as a second addition to FIG. 1 a perspective view of the filling device 1 with view from the rear side of the sight glass towards recess 51 and the bayonet groove 81 with the thread pitch 91.

Figure 2:
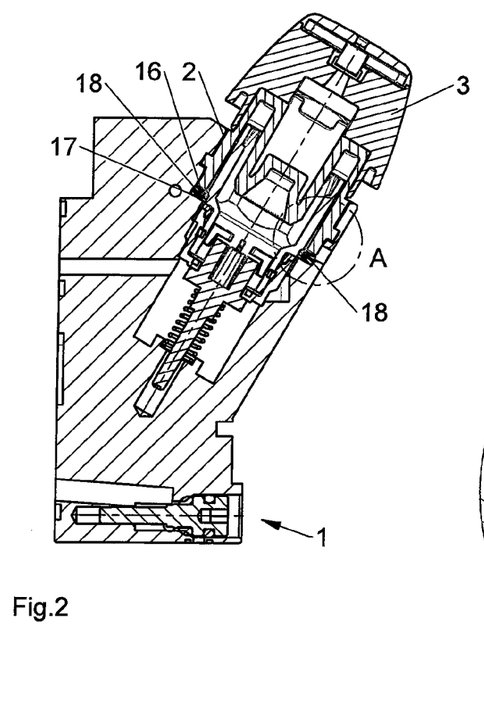
FIG. 2 is a sectional view of the filling device according to FIG. 1.
Figure 2A:
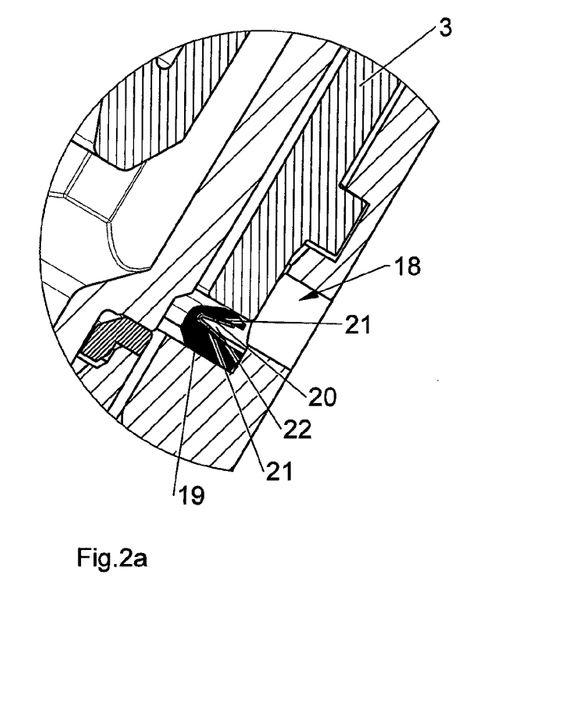
FIG. 2a is a detail "A" according to FIG. 2.

FIG. 2 illustrates the filling device 1 according to FIG. 1 in a longitudinal section. Identical components are designated by the same reference numbers as in FIG. 1. A ring seal 18, which consists of a sealing material 19 with a V-shaped spring element 20 located on the inside, is located between a front side 16 of the closing element 3 and a contact surface 17 on the underside of the filler neck 2. FIG. 2a shows detail "A" according to FIG. 2 with an enlarged view of the spring element 20. The closing element 3 has a ring seal engagement portion comprising a leading edge side of the closing element as shown in FIG. 2a. As shown in FIG. 2a, the leading edge side of the closing element 3 is a part of the closing element 3 at a farthest distance into the filler neck 2, with the closing element 3 attached to the filler neck. When the closing element 3 is rotated from the first position 10 into the second position 11, the legs 21 of the spring element 20 are pressed against each other and pressed axially due to the thread pitch 9 of the bayonet grooves 8, as a result of which the closing element 3 is sealed against the filler neck 2 by means of the sealing material 19. The free space 22 between the legs 21 decreases during the axial pressing of the ring seal 18.

Figure 3:
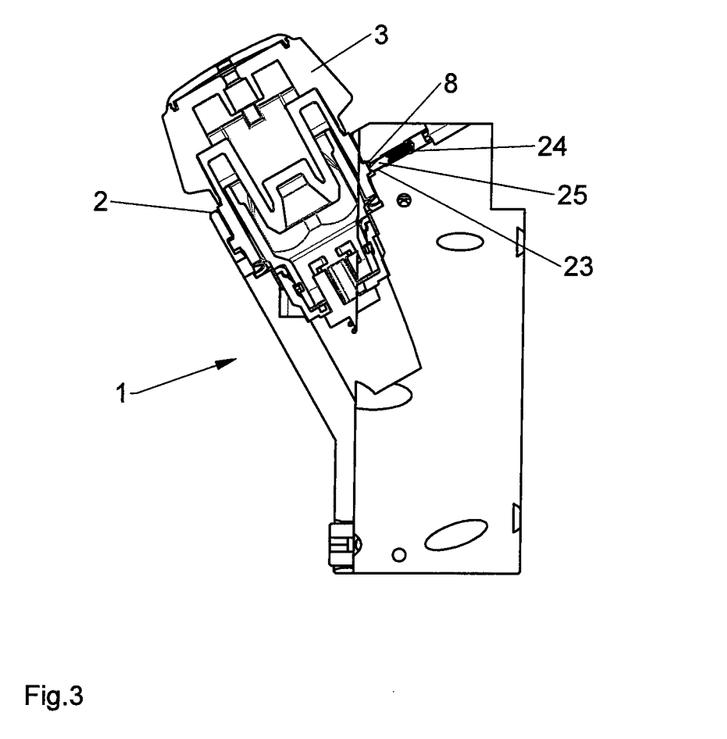
FIG. 3 is a sectional view corresponding to FIG. 2 with an acoustic signal generator.

FIG. 3 shows a sectional view of the filling device 1 rotated by 180 degrees relative to FIG. 2. A contact element in the form of a pin 25, which is prestressed by a compression spring 24 and is arranged within the bayonet groove 8, is located in a hole 23.

Figure 4:
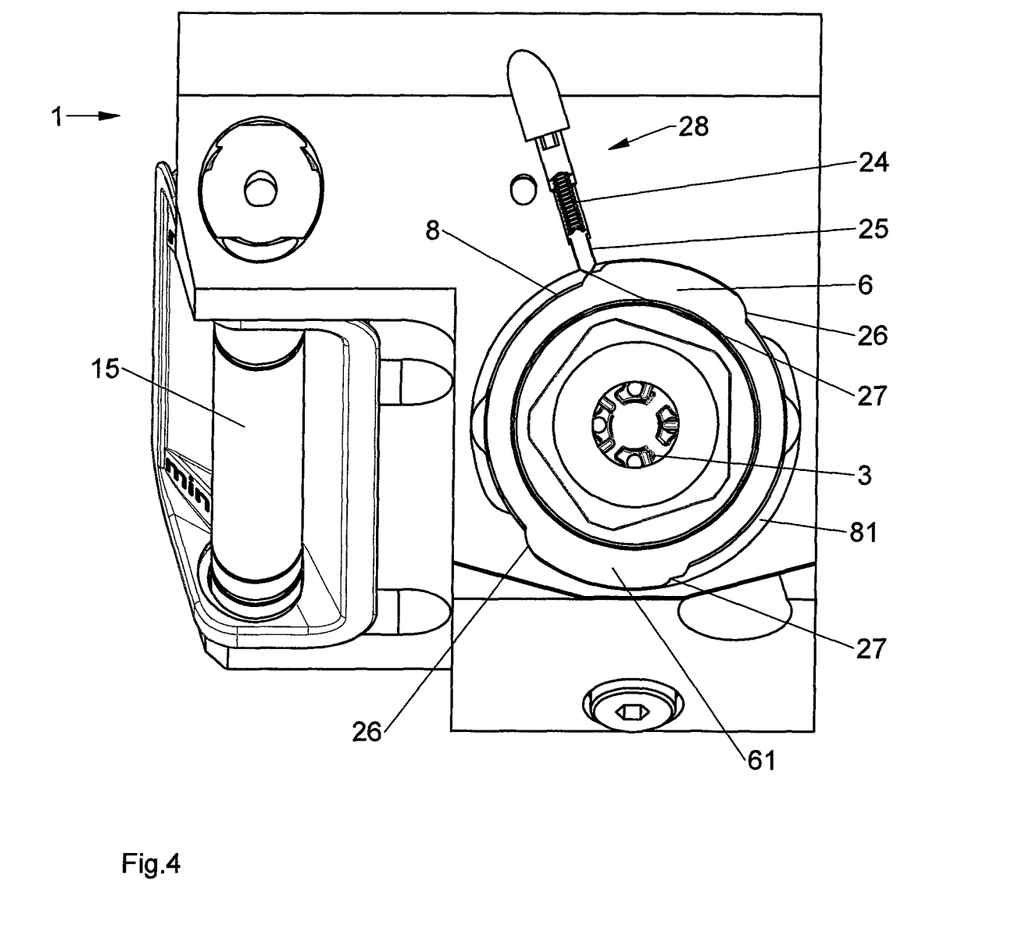
FIG. 4 is a top partially sectional view of the filler neck.

FIG. 4 shows a sectional view of the filling device 1 with a top view of the pin 25 and the bayonet cams 6, 61 within the bayonet grooves 8, 81. The bayonet grooves 8, 81 have stop faces 26, with which the bayonet cams 6 are in contact in the second position 11 of the closing element 3. Step-like depressions 27, which touch the pin 25 during the transition into the second position 11, are located on the side of the bayonet cams 6, 61 facing away from the stop faces 26. A "clicking sound," which indicates to the user that the blocked position has been reached, is generated by the cooperation of the pin 25 prestressed with the compression spring 24 with one of the depressions 27, which together form an acoustic signal generator 28 that is a preferred signaling means for acoustic signal generation when the second position is reached.

While specific embodiments of the invention have been shown and described in detail to illustrate the application of the principles of the invention, it will be understood that the invention may be embodied otherwise without departing from such principles.

| List of Reference Numbers | |
|---|---|
| 1 | Filling device |
| 2 | Filler neck |
| 3 | Closing element |
| 4 | Inner wall |
| 5 | Recess |
| 51 | Recess |
| 6 | Bayonet cam |
| 61 | Bayonet cam |
| 7 | Straight pin |
| 8 | Bayonet groove |
| 81 | Bayonet groove |
| 9 | Thread pitch |
| 91 | Thread pitch |
| 10 | First position |
| 11 | Second position |
| 12 | Actuating knob |
| 13 | Grip surface |
| 14 | Rectangular surface |
| 15 | Sight glass |
| 16 | Front side |
| 17 | Contact surface |
| 18 | Ring seal |
| 19 | Sealing material |
| 20 | Spring element |
| 21 | Leg |
| 22 | Free space |
| 23 | Hole |
| 24 | Compression spring |
| 25 | Pin |

-continued

List of Reference Numbers

| 26 | Stop face |
| 27 | Depression |
| 28 | Acoustic signal generator |
| 29 | Bayonet catch |

What is claimed is:

1. A filling device for an anesthetic dispenser, the filling device comprising:
a filler neck, for filling the anesthetic dispenser with liquid anesthetic, with a thread part and with recesses;
a closing element for attachment to the filler neck with a complementary thread part for cooperating with the thread part to form a threaded connection providing relative axial movement between the closing element and the filler neck upon rotary motion of the closing element relative to the filler neck during thread engagement between the thread part and the complementary thread part, the threaded connection comprising a rotatingly movably actuatable bayonet catch comprising bayonet grooves as the thread part and bayonet cams as the complementary thread part;
a ring seal provided between the closing element and the filler neck, the ring seal having an expanded state and a pressed state upon being pressed between the closing element and the filler neck by the axial movement; and
an elastically deformable spring element biasing the ring seal toward the expanded state, wherein:
the closing element is plugable into the filler neck with the bayonet cams being inserted into the respective recesses to reach a first position and is rotatable into a second position as a blocked position by the rotary motion; and
the closing element has a toggle-like actuating knob in a position fixed relative to the bayonet cams, the toggle-like actuating knob indicating a preferred position of the closing element relative to the recesses of the filler neck and further comprising:
a signaling means for acoustic signal generation when the second position is reached.

2. A filling device in accordance with claim 1, wherein the spring element has a V-shaped or U-shaped or helical or plate-like design on one side.

3. A filling device in accordance with claim 1, wherein the ring seal is arranged between a front leading edge side of the closing element and a contact surface at the filler neck.

4. An anesthetic dispenser filling device comprising:
a filler neck for filling the device with liquid anesthetic, the filler neck having a thread part and having filler neck recesses extending in an axial direction;
a closing element for attachment to the filler neck with a complementary thread part for cooperating with the thread part to form a threaded connection, the threaded connection comprising a rotatingly movably actuatable bayonet catch including bayonet grooves of the filler neck and bayonet cams on the closing element, the threaded connection providing a defined relative axial movement between the closing element and the filler neck upon rotary motion of the closing element relative to the filler neck during engagement between the bayonet catch and the bayonet groove; and
a ring seal with a closing element engaging surface and a filler neck engaging surface, the ring seal being provided between a closing element ring seal engagement portion and a filler neck ring seal engagement portion, neck, the ring seal having an expanded state with the closing element engaging surface spaced apart from the filler neck engaging surface by an expanded distance and having a pressed state with the closing element engaging surface spaced apart from the filler neck engaging surface by a pressed distance, with the pressed distance being smaller than the expanded distance, upon the ring seal being pressed between the closing element ring seal engagement portion and the filler neck ring seal engagement portion by the axial movement;
an elastically deformable spring element biasing the ring seal toward the expanded state, wherein:
the recesses each have a design corresponding to the bayonet cams and each receive one of the bayonet cams to allow the closing element to be plugged, in the axial direction, into the filler neck, to reach a plugged in first position;
the bayonet grooves and the bayonet cams define a blocked second position in which further rotary motion of the closing element relative to the filler neck is blocked;
the closing element is rotatable from the first position into the second position providing the defined relative axial movement between the closing element ring seal engagement portion and the filler neck ring seal engagement portion;
the closing element comprises a toggle shaped actuating knob in a fixed position relative to the bayonet catches, the toggle shaped actuating knob providing an indication of a position of the bayonet catches relative to the bayonet grooves for plugging the closing element into the filler neck at the first position;
the bayonet groove and the bayonet catch form a stop face defining the blocked second position and further comprising:
an acoustic sound generator generating a sound when the second position is reached wherein the sound generator comprises a contact element contacting one of the bayonet cams and changing position and generating the sound upon the closing element reaching the stop face.

5. An anesthetic dispenser filling device in accordance with claim 4, wherein:
the ring seal has at least one of a V-shaped, U-shaped, helical and plate-like cross section; and
the spring element has at least one of a V-shaped, U-shaped, helical and plate-like cross section.

6. An anesthetic dispenser filling device in accordance with claim 4, wherein the ring seal is arranged between a front leading edge side of the closing element, forming the closing element ring seal engagement portion, and a contact surface at the filler neck, forming the filler neck ring seal engagement portion, the leading edge side of the closing element being the side of the closing element that extends the farthest into the filler neck upon the closing element being attached to the filler neck.

7. An anesthetic dispenser filling device in accordance with claim 4, wherein
the elastically deformable spring element is formed of a metal or an anesthetic-resistant plastic; and
the ring seal is formed of sealing material comprising one or more polymers.

8. An anesthetic dispenser filling device comprising:
a filler neck for filling the device with liquid anesthetic, the filler neck having a thread part and having filler neck recesses extending in a plug in direction;
a closing element for attachment to the filler neck with a complementary thread part for cooperating with the thread part to form a threaded connection, the threaded connection comprising a rotatingly movably actuatable bayonet catch including bayonet grooves of the filler neck as the thread part and bayonet cams of the closing element as the complementary thread part, the threaded connection having a thread pitch providing a defined relative axial movement between the closing element and the filler neck upon rotary motion of the closing element relative to the filler neck during engagement between the bayonet catch and the bayonet groove;

a ring seal with a closing element engaging surface and a filler neck engaging surface, the ring seal being provided between a closing element ring seal engagement portion and a filler neck ring seal engagement portion, the closing element ring seal engagement portion comprising a leading edge side of the closing element, the leading edge side of the closing element being at a farthest distance into the filler neck with the closing element attached to the filler neck, the ring seal having an expanded state with the closing element engaging surface spaced apart from the filler neck engaging surface by an expanded distance and having a pressed state with the closing element engaging surface spaced apart from the filler neck engaging surface by a pressed distance, with the pressed distance being smaller than the expanded distance, upon the ring seal being pressed between the closing element ring seal engagement portion and the filler neck ring seal engagement portion by the axial movement; and an elastically deformable spring element biasing the closing element toward the expanded state, wherein:

the recesses each have a design corresponding to the bayonet cams and each receive one of the bayonet cams to allow the closing element to be plugged, in the plug in direction, into the filler neck, to reach a plugged in first position;

the bayonet grooves and the bayonet cams define a blocked second position in which further rotary motion of the closing element relative to the filler neck is blocked;

the closing element is rotatable from the first position into the second position providing the defined relative axial movement between the closing element ring seal engagement portion and the filler neck ring seal engagement portion; and the closing element comprises a toggle shaped actuating knob in a fixed position relative to the bayonet catches and providing an indication of a position of the bayonet catches relative to the bayonet grooves for plugging the closing element into the filler neck at the first position; and the bayonet groove and the bayonet catch form a stop face defining the blocked second position and further comprising an acoustic sound generator generating a sound when the second position is reached, wherein the sound generator comprises a contact element which experiences a change in position upon one of the filler neck and the closing element reaching the stop face.

9. An anesthetic dispenser filling device in accordance with claim 8, wherein:

the ring seal has at least one of a V-shaped, U-shaped, helical and plate-like cross section; and the spring element has at least one of a V-shaped, U-shaped, helical and plate-like cross section.

\* \* \* \* \*